US009107838B2

(12) United States Patent
Stookey et al.

(10) Patent No.: US 9,107,838 B2
(45) Date of Patent: Aug. 18, 2015

(54) FLUORIDE VARNISH

(71) Applicant: THERAMETRIC TECHNOLOGIES, INC., Indianapolis, IN (US)

(72) Inventors: George K. Stookey, Indianapolis, IN (US); Christopher J. Herron, Spartanburg, SC (US); Richard A. Krone, Maple Glen, PA (US); Jerome E. Swanson, St. Paul, MN (US)

(73) Assignees: Therametrics Technologies, Inc., Noblesville, IN (US); Elevate Oral Care, LLC, West Palm Beach, FL (US)

( * ) Notice: Subject to any disclaimer, the term of this patent is extended or adjusted under 35 U.S.C. 154(b) by 0 days.

(21) Appl. No.: 14/181,050

(22) Filed: Feb. 14, 2014

(65) Prior Publication Data

US 2014/0162208 A1 Jun. 12, 2014

Related U.S. Application Data

(63) Continuation-in-part of application No. 13/868,822, filed on Apr. 23, 2013.

(60) Provisional application No. 61/637,928, filed on Apr. 25, 2012.

(51) Int. Cl.
  *A61K 8/21* (2006.01)
  *A61K 8/24* (2006.01)
  *A61Q 11/00* (2006.01)
  *A61C 19/06* (2006.01)
  *A61K 8/365* (2006.01)
  *A61K 8/98* (2006.01)

(52) U.S. Cl.
  CPC ................ *A61K 8/21* (2013.01); *A61C 19/063* (2013.01); *A61K 8/365* (2013.01); *A61K 8/987* (2013.01); *A61Q 11/00* (2013.01); *A61K 2800/87* (2013.01)

(58) Field of Classification Search
  USPC .......................................... 424/52, 486, 601
  See application file for complete search history.

(56) References Cited

U.S. PATENT DOCUMENTS

| | | |
|---|---|---|
| 4,134,935 A | 1/1979 | Quiring et al. |
| 4,797,431 A | 1/1989 | Billington et al. |
| 4,837,007 A | 6/1989 | Duckworth et al. |
| 4,883,534 A | 11/1989 | Sandham et al. |
| 5,049,375 A | 9/1991 | Tsujita et al. |
| 5,178,870 A | 1/1993 | Schaeken et al. |
| 5,213,615 A | 5/1993 | Michl |
| 5,294,207 A | 3/1994 | Keating et al. |
| 5,395,241 A | 3/1995 | Kandelman |
| 5,648,399 A | 7/1997 | Friedman et al. |
| 5,716,104 A | 2/1998 | Keating et al. |
| 5,885,552 A | 3/1999 | Causton |
| 5,989,522 A | 11/1999 | Friedman |
| 5,993,413 A | 11/1999 | Aaltonen et al. |
| 6,083,421 A | 7/2000 | Huang et al. |
| 6,093,084 A | 7/2000 | Jefferies |
| 6,217,851 B1 | 4/2001 | Kleinberg et al. |
| 6,395,259 B1 | 5/2002 | Shalaby |
| 6,506,053 B2 | 1/2003 | Wiesel |
| 6,524,559 B2 | 2/2003 | Urai et al. |
| 6,537,360 B2 | 3/2003 | Miyama et al. |
| 6,652,280 B2 | 11/2003 | Cohen |
| 6,729,878 B2 | 5/2004 | Cohen et al. |
| 7,264,882 B2 | 9/2007 | Engelbrecht |
| 7,300,645 B2 | 11/2007 | Takatsuka et al. |
| 7,335,691 B2 | 2/2008 | Orlowski et al. |
| 7,387,774 B2 | 6/2008 | Faller et al. |
| 7,491,694 B2 | 2/2009 | Reynolds et al. |
| 7,507,047 B2 | 3/2009 | Oberstadt et al. |
| 7,563,833 B2 | 7/2009 | Orlowski et al. |
| 7,803,353 B2 | 9/2010 | Lee et al. |
| 7,842,749 B2 | 11/2010 | Shalaby et al. |
| 7,846,411 B2 | 12/2010 | Tung |
| 7,862,801 B2 | 1/2011 | Chen |
| 2003/0183124 A1 | 10/2003 | Engelbrecht |
| 2005/0175552 A1* | 8/2005 | Hoic et al. ...................... 424/49 |
| 2006/0134012 A1 | 6/2006 | Symington et al. |
| 2006/0204452 A1 | 9/2006 | Velamakanni |
| 2007/0003493 A1 | 1/2007 | Simonton et al. |
| 2007/0041913 A1 | 2/2007 | Urai et al. |
| 2007/0183986 A1 | 8/2007 | Allred |
| 2007/0202342 A1 | 8/2007 | Whiteford et al. |
| 2008/0107612 A1 | 5/2008 | Simonton et al. |
| 2008/0119588 A1 | 5/2008 | Orlowski |
| 2008/0187500 A1 | 8/2008 | Karlinsey |

(Continued)

FOREIGN PATENT DOCUMENTS

| | | |
|---|---|---|
| EP | 0400641 A1 | 12/1990 |
| EP | 0897709 A1 | 2/1999 |
| EP | 0900560 A1 | 3/1999 |
| EP | 1 666 019 | 6/2006 |
| WO | WO 2009/124311 A1 | 10/2009 |

OTHER PUBLICATIONS

B.-T. Hoang-Dao, et al., "Clinical efficiency of a natural resin fluoride varnish (Shellac F) in reducing dentin hypersensitivity," *Journal of Oral Rehabilitation* 2009, vol. 36; pp. 124-131; 8 pages.
Bioactive Materials for Advanced Oral Health, ACTIV™ Varnish, received by the applicant prior to Apr. 24, 2012.
Pulpdent Activ Varnish, Cumulative Fluoride Release of Leading Fluoride Varnishes, received by the applicant prior to Apr. 24, 2012.
International Search Report issued by the Korean Intellectual Property Office, dated Aug. 19, 2013, for International Application No. PCT/US2013/037817; 3 pages.

(Continued)

*Primary Examiner* — Walter Webb
(74) *Attorney, Agent, or Firm* — Faegre Baker Daniels LLP

(57) ABSTRACT

A tooth varnish that is free from pinus extracts, free of substantial undesired coloring agents, with a reduced viscosity, delivered in a user-friendly, flow-through, unit dose applicator and having improved fluoride release, uptake, and remineralization properties.

20 Claims, 1 Drawing Sheet

(56) References Cited

U.S. PATENT DOCUMENTS

| | | |
|---|---|---|
| 2008/0292565 A1 | 11/2008 | Tung |
| 2008/0299520 A1 | 12/2008 | Ali et al. |
| 2008/0305457 A1 | 12/2008 | Ali et al. |
| 2009/0022672 A1 | 1/2009 | Reynolds |
| 2009/0142282 A1 | 6/2009 | Kendall et al. |
| 2009/0191279 A1 | 7/2009 | Kennard et al. |
| 2009/0324516 A1 | 12/2009 | Muscle et al. |
| 2010/0215593 A1 | 8/2010 | Reynolds et al. |
| 2010/0247456 A1 | 9/2010 | Niederman et al. |
| 2010/0254918 A1 | 10/2010 | Maryska et al. |
| 2010/0260849 A1* | 10/2010 | Rusin et al. ............... 424/486 |
| 2010/0285424 A1 | 11/2010 | Burgio et al. |
| 2010/0316726 A1 | 12/2010 | Prencipe et al. |
| 2011/0033394 A1 | 2/2011 | Blanvalet et al. |
| 2011/0076241 A1 | 3/2011 | Kato et al. |
| 2011/0097368 A1 | 4/2011 | Jensen et al. |
| 2012/0020899 A1 | 1/2012 | Zaidel et al. |
| 2013/0149391 A1 | 6/2013 | Wagner et al. |
| 2014/0065079 A1 | 3/2014 | To et al. |

OTHER PUBLICATIONS

Written Opinion issued by the Korean Intellectual Property Office, dated Aug. 16, 2013, for International Application No. PCT/US2013/037817; 9 pages.

International Preliminary Report on Patentability issued by the International Bureau of WIPO, Geneva, Switzerland, dated Oct. 28, 2014 for International Application No. PCT/US2013/037817; 12 pages.

International Search Report and Written Opinion issued by the Korean Intellectual Property Office, dated Nov. 17, 2014, for International Application No. PCT/US2014/016507; 17 pages.

* cited by examiner

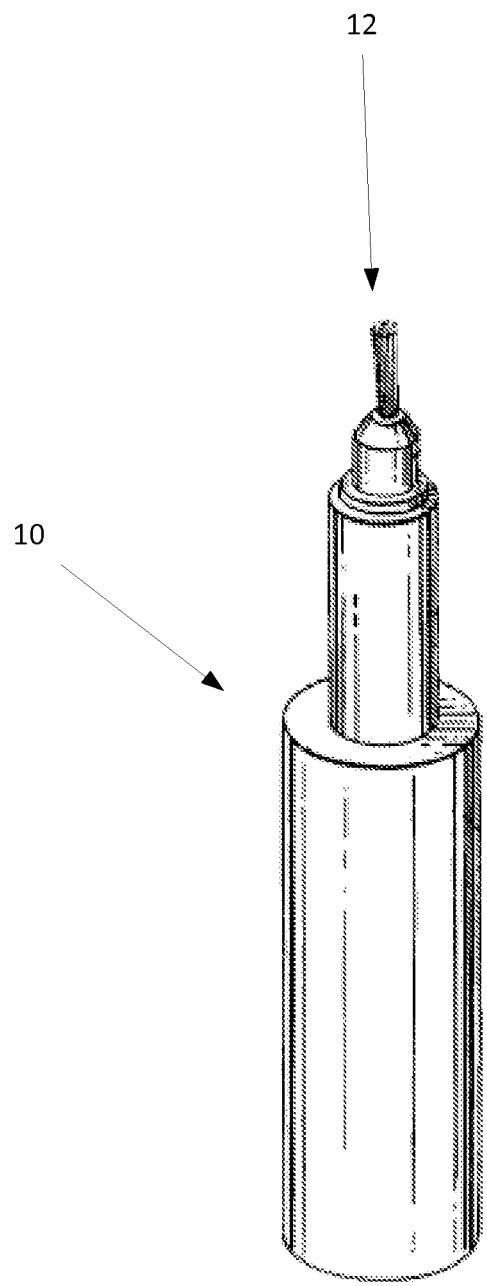

FLUORIDE VARNISH

PRIORITY

The present application is a Continuation-In-Part application of U.S. Non-Provisional application Ser. No. 13/868,822, filed Apr. 23, 2013, that is a non-provisional of U.S. Provisional application Ser. No. 61/637,928, filed on Apr. 25, 2012, the disclosures of which are hereby expressly incorporated by reference and priority is claimed thereto.

FIELD

The present disclosure relates generally to an oral treatment. More specifically, the present disclosure relates to a varnish that provides for increased uptake of fluoride in enamel.

BACKGROUND AND SUMMARY

Fluoride varnish is a highly concentrated form of fluoride which is applied to the tooth's surface, by a dentist, dental hygienist or other health care professional, as a type of topical fluoride therapy. It is not a permanent varnish but due to its adherent nature it is able to stay in contact with the tooth surface for several hours. It may be applied to the enamel, dentin or cementum of the tooth and can be used to help prevent decay, remineralize the tooth surface, and to treat dentine hypersensitivity.

Fluoride-containing varnishes were originally developed some 50 years ago as a material for application by dentists to control dentinal hypersensitivity (i.e., pain to temperature changes and touch) in patients by occluding exposed dentinal tubules. In the 1960's scientists in Europe began adding 5% sodium fluoride to the varnishes to enhance their activity by precipitating calcium fluoride on the exposed tubules along with the varnish. Additional clinical studies in Europe demonstrated that these fluoride-containing varnishes also were effective for the prevention of dental caries through the release of fluoride even though their retention on the enamel surface was generally less than 24 hours. As a result of these studies fluoride varnishes are now used throughout the world for both caries prevention and the treatment of dentinal hypersensitivity.

The effectiveness of a topical fluoride (such as a varnish) is primarily a function of the amount of fluoride uptake that can be achieved in previously demineralized areas. Fluoride uptake is affected by the concentration of fluoride in the formula, the amount of time that the varnish is in contact with the demineralized area, and the ability of the varnish to induce migration of the fluoride from the varnish to the dental tissue.

With respect to the concentration of fluoride in the varnish, increased concentrations of fluoride also come with increased risks of dental fluorosis. This risk is especially pronounced and concerning for pediatric patients. Accordingly, simply providing a higher concentration of fluoride in the varnish is not always desired nor inherently superior.

Fluoride varnish is composed of a high concentration of fluoride in a fast drying (or curing), alcohol and rosin based solution. Existing varnishes are known to have 5.0% sodium fluoride. The rosin base is made of pine tree origin (e.g. colophonium or a derivative thereof). This rosin provides allergic responses in some patients. Additionally, the rosin has a yellow tint. When applied to teeth, this yellow tint is undesirable and unsightly. More recently derivatized (hydrogenated and other) versions have become readily available and used frequently. These varnishes have little color.

Additionally, many existing varnishes, when applied, have a film thickness that is detectable to a patient. This thickness is noticeable and objectionable to the touch of the tongue. In addition, most existing varnishes are organoleptically unacceptable, especially for pediatric patients.

Existing varnishes that contain sodium fluoride contain little or no water (<5%). Since the fluoride is not easily soluble in these formulas, the fluoride normally settles and precipitates in these formulas. Sodium fluoride is an inorganic chemical compound that is soluble in water. Compositions such as consumer use dentifrices and oral rinses as well as professional use foams and gels containing fluoride contain water. These embodiments allow the fluoride to be evenly dispersed and therefore provide uniform deposition onto tooth surfaces. However, since these compositions begin breaking down immediately when introduced into the oral cavity, long term retention is not possible.

The physical irritants of discoloration and objectionable feel are factors that tend to lead patients to reducing the amount of time that the varnish is permitted to act. In the case of the yellowing tint, this reduces patient likelihood to use the product in the first place and also increases the likelihood that the varnish will be prematurely removed. Similarly, the physical uncomfortability from film thickness increases the likelihood that the varnish will be removed prematurely, either voluntarily or through increased friction from being rubbed by the tongue.

Existing varnishes also suffer from separation of their ingredients during storage. Fluoride particles settle out of the mixture creating a non-homogeneous paste. U.S. Pat. No. 7,563,833 to Orlowski recognizes the difficulty in retaining fluoride salts in suspension in dental varnish. Typically, fluoride varnishes are now marketed in unit dose packages that are mixed by stirring and immediately applied with a small brush covering all of the tooth surfaces. This mixing is required due to the settling out of the ingredients. Patients are instructed not to brush their teeth for at least 4 hours (to prolong retention of the varnish) and are advised that the varnish will be gone within 24 hours or less.

Accordingly, what is needed is a varnish that does not induce a pine allergy, does not impart an unsightly yellow tint to the dental tissue, has acceptable taste properties, is of a thickness that is unnoticeable, has a fluoride concentration that reduces likelihood of dental fluorosis, has a prolonged retention time on the dental tissue, resists settling out of ingredients, and provides superior fluoride release and uptake in tooth tissue.

Additional features of the present disclosure will become apparent to those skilled in the art upon consideration of the following detailed description of the presently perceived best mode of carrying out the disclosure.

BRIEF DESCRIPTION OF THE DRAWING

The detailed description particularly refers to the accompanying figures in which:

FIG. 1 is a perspective view of an applicator suitable for applying varnish according to embodiments of the present disclosure.

DETAILED DESCRIPTION

According to one exemplary embodiment of the present disclosure (the "first embodiment"), a varnish is provided that is made up of:

30% Bleached dewaxed shellac (from insect-derived lac);
2.5% Sodium Fluoride;

58.8% Ethanol;
1% Citric Acid;
3% Flavoring;
2% Ammonium Phosphate;
2% Xylitol;
0.6% Sodium Saccharin; and
0.10% Hydroxyapatite/Calcium Phosphate.

While the above formulation lists specific quantities, it should be appreciated that embodiments are anticipated where deviations on the percentages of each ingredient are made. One of skill in the art will recognize that such deviations in percentages or additions of other ingredients in small amounts are within the scope of the disclosure.

In one embodiment, the varnish is provided in a flow-through unit-dose applicator such as ampule 10 having a brush applicator 12 present at an egress point thereof as shown in FIG. 1. One such applicator is described in U.S. Pat. No. 5,716,104. The ampule is illustratively constructed from pliable plastic. Squeezing the ampule provides for egress of the varnish from the ampule and into the brush. The brush is then put into contact with dental tissue (enamel) to apply the varnish thereto. It should be appreciated that the varnish is of a suitable viscosity to allow movement through the brush and to be responsive to the applied squeezing pressure. As will be discussed below, the reduced viscosity of the varnish is achieved through certain ingredient choices.

The Sodium Fluoride is provided having an average particle size (diameter) of less than 50 micrometers (microns). Further embodiments are provided where at least 80% of the particles have a diameter of less than 16 microns. The fluoride is milled to obtain these particle sizes. Tight tolerances on the particle size provide for consistent fluoride release properties. Furthermore, smaller fluoride particles decrease the likelihood of the particles settling out of solution. Additionally, smaller fluoride particles provide for increased ease of re-suspension thereof when some fluoride does happen to settle out. In addition to formulations having 2.5% sodium fluoride, embodiments are envisioned having greater amount of sodium fluoride, such as 5%. Indeed, formulations are envisioned having 1%-7.5% fluoride by weight.

Still further, embodiments are envisioned where crystalline Sodium Fluoride is used where all or nearly all (such as greater than 90%, 95%, or 99%) of the fluoride particles are less than 20±2 microns in diameter. Still further, in addition to using milling to obtain these particle sizes, sifting or sieving is also (or alternatively) used.

As previously noted, traditional varnishes have relied on pine tree rosin base. In order to remove the potential for pine allergy, the present varnish uses the bleached dewaxed shellac (lac). This shellac is a non-water soluble dewaxed, bleached shellac. This shellac, when applied, is colorless or clear such that no color is applied to the teeth thereby. Accordingly, the present varnish does not present an unsightly appearance. Ethanol is provided as a solvent for the lac. Embodiments having between 5-40% shellac (by weight) have been formulated that provide usable varnishes. Embodiments having 10-40% (more specifically 25-35%) shellac have exhibited more desirable properties. Whereas too great of a shellac content creates a thick and noticeable coating, too low of a shellac content imparts low viscosity which can allow the varnish to migrate off the tissue to which it is applied and onto surrounding tissues, such as gingival tissues. Furthermore, the viscosity is chosen to allow the varnish to respond to pressure applied to the flow-through unit dose ampule and impregnate brush while also allowing the varnish to release from brush onto enamel. A varnish of 30% shellac is found to sufficiently inhibit undesired varnish migration to the surrounding tissues. The present formulation has a viscosity of 30-60 centipoise. Embodiments are envisioned having a viscosity of less than 100 centipoise and more specifically less than 75 centipoise.

Monobasic ammonium phosphate (MAP) was added and resulted in enhanced fluoride release and enhanced fluoride uptake by the underlying enamel. MAP is an inorganic phosphate. While MAP is specifically discussed, other embodiments that use other inorganic phospates are anticipated. Traditional varnishes have included an organic system including colophonium and alcohol in which traditional water-soluble inorganic ortho-phosphates (such as MAP), are totally (or nearly totally) insoluble. Similarly, dibasic sodium and potassium phosphates are only slightly soluble in alcohol while other water soluble phosphates such as sodium and potassium pyrophosphates, sodium glycerophosphate and sodium hexametaphosphate are also insoluble in alcohol. The present varnish is similarly an organic system in which MAP is only slightly soluble. Accordingly, it was surprising that the addition of phosphate to an organic product would provide any benefit to the non-aqueous varnish. However, it was consistently demonstrated that the presence of phosphate significantly increased the amount of fluoride released when immersed in an aqueous environment (such as a mouth). Testing shown in Table 1 shows that a concentration of somewhere between 1-3% resulted in the greatest fluoride release properties.

TABLE 1

| Ammonium Phosphate percent | Fluoride Release (micrograms F/grams varnish) |
| --- | --- |
| 0.0 | 4,384 ± 114 |
| 1.0 | 5,072 ± 387 |
| 2.0 | 5,518 ± 314 |
| 3.0 | 4,646 ± 108 |

MAP presents slight solubility in ethyl alcohol and acidic pH. Embodiments are envisioned where sodium and potassium salts are used instead of MAP.

Additionally, the inclusion of MAP also had the unexpected result of aiding in the re-suspension of settled sodium fluoride. In the absence of the phosphate, the sodium fluoride settles to the bottom or sides of the delivery ampule over a period of several hours and becomes difficult to re-suspend. This settling out of the fluoride is exacerbated by the relatively low viscosity of the varnish. The presence of MAP facilitated the re-suspension of the sodium fluoride within 10 seconds of reasonable manual shaking of the ampule.

Citric Acid was added to enhance the retention of the varnish by slightly etching sound enamel on which the varnish is applied. Citric Acid is a carboxylic acid. Retention is less of a concern in areas having sensitivity problems due to exposed dentinal tubules and areas having demineralization providing suitable bonding sites for the varnish. However, sound enamel surfaces are more challenging on which to achieve suitable bonding for the varnish. The slight etching of the enamel by the citric acid improves adherence (retention) of the varnish, including on areas of sound enamel. Increased adherence (retention) results in increased caries-preventive effects. Embodiments having 5% or less citric acid have been formulated that provide usable varnishes. Embodiments having 1-3% citric acid have exhibited suitable properties. Embodiments are envisioned where other carboxylic acids are used in place of the citric acid. It should be appreciated that citric acid and carboxylic acids in general are known sequestering agents.

Hydroxyapatite/Tricalcium Phosphate enhances the deposition of fluoride and the remineralization of demineralized enamel for so long as the fluoride does not react with the calcium prior to delivery to the enamel surface. As previously noted, the varnish presents a non-aqueous mixture. The non-aqueous mixture keeps the fluoride separated from the calcium within the varnish. Accordingly, the provided combination of elements causes the fluoride to remain in a non-dissolved/non-dissociated form prior to application. Once applied, the aqueous environment of the mouth allows interaction between the fluoride and the calcium with the tooth surfaces.

Various taste additives (xylitol, sodium saccharin, and flavoring) were added to increase the taste appeal, particularly for children.

The above embodiment includes 58.8% Ethyl Alcohol. Embodiments are envisioned where at least 38% of the varnish is Ethyl Alcohol. More specifically, embodiments of up to 90% alcohol are envisioned. This concentration of alcohol allows the varnish to be a liquid mixture. Traditional varnishes have been pastes and not water soluble.

The above varnish was tested along with the leading commercially available varnishes. The above varnish formulation having 5% sodium fluoride exhibited 13,205±197 micrograms of fluoride release per gram of varnish. The largest amount of fluoride release of the other tested varnishes was 11,480±286 micrograms of fluoride per gram of varnish.

According to a second exemplary embodiment of the present disclosure, a varnish is provided that is made up of:
  30% Dewaxed shellac (from insect-derived lac);
  2.5% Sodium Fluoride;
  59.8% Ethanol;
  2.5% Flavoring;
  2.0% Anhydrous Dibasic Sodium Phosphate, ($Na_2HPO_4$,);
  1.9% Xylitol;
  1.2% Anhydrous Sucralose; and
  0.10% Hydroxyapatite/Calcium Phosphate.

The second embodiment differs from the first in the deletion of the citric acid due (at least partially) to the excellent enamel retention properties of the shellac. The second embodiment further uses anhydrous dibasic sodium phosphate instead of acidic ammonium phosphate. Also, sucralose is used instead of saccharin. Embodiments are envisioned where other chemically suitable sweeteners are used.

It should be appreciated that the deletion of the citric acid and the use of anhydrous dibasic sodium phosphate provide an alkaline environment as opposed to the acidic environment described with respect to the first embodiment. Accordingly, the varnish has an overall pH of greater than 7. Furthermore, it should be appreciated that while specific percentages of ingredients are listed, small variations can be made thereto and still be within the scope of this disclosure.

Additionally, whereas the first embodiment used bleached dewaxed insect-derived shellac, the second embodiment does not use "bleached" shellac. Rather, in one illustrated embodiment, de-colored shellac and/or shellac that has undergone solvent extraction is used. In one embodiment, shellac processed as follows. Shellac is first dissolved in ethanol. Impurities and shellac wax are removed by filtration. Subsequently, the shellac solution is decolorized by addition of activated carbon. After removal of the activated carbon by a second filtration, the solvent is evaporated in a thin film evaporator and recovered. Removal of the solvent increases the concentration of the shellac solution until a hot molten shellac mass is obtained which is cast into a film. After cooling, the film breaks into shellac flakes. However, it should be appreciated that use of other shellacs and processes are envisioned where such shellacs do not impart noticeable and undesired tints to teeth when applied. Furthermore, wherever one type of shellac is described here (bleached and/or de-colored) embodiments are envisioned that use a differing kind of shellac. Still further, as previously discussed, the present embodiments do not contain rosin, pine-based or otherwise.

The above second-embodiment varnish was tested along with the leading commercially available varnishes. The second-embodiment varnish formulation exhibiting superior fluoride release. Indeed, the second-embodiment varnish released over 95% of the fluoride contained thereby within four hours of application. The largest amount of fluoride release at the four-hour mark of the other tested varnishes was 38% of the fluoride contained therein.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

The invention claimed is:

1. A tooth coating composition comprising:
  shellac;
  monobasic ammonium phosphate; and
  fluoride, the composition being devoid of rosin, the composition having a viscosity between 30-60 centipoise.

2. The composition of claim 1, further comprising alcohol.

3. The composition of claim 2, wherein the content of the alcohol is in a range of 38%-90% by weight.

4. The composition of claim 1, wherein the content of the shellac is in a range of 5-40% by weight.

5. The composition of claim 4, wherein the content of the shellac is in a range of 25-35% by weight.

6. The composition of claim 1, wherein the composition is devoid of *pinus* extracts.

7. The composition of claim 1, wherein the fluoride is sodium fluoride.

8. The composition of claim 1, wherein the amount of fluoride is less than 5% by weight.

9. The composition of claim 1, further including a sweetener.

10. The composition of claim 1, wherein the shellac is insect-derived lac.

11. A tooth coating composition comprising:
  shellac;
  monobasic ammonium phosphate; and
  fluoride, the composition having a viscosity between 30-60 centipoise.

12. The composition of claim 11, further comprising alcohol.

13. The composition of claim 12, wherein the content of the alcohol is in a range of 38%-90% by weight.

14. The composition of claim 11, wherein the content of the shellac is in a range of 5-40% by weight.

15. The composition of claim 14, wherein the content of the shellac is in a range of 25-35% by weight.

16. The composition of claim 11, wherein the composition is devoid of pinus extracts.

17. The composition of claim 11, wherein the fluoride is sodium fluoride.

18. The composition of claim 11, wherein the amount of fluoride is less than 5% by weight.

19. The composition of claim 11, further including a sweetener.

20. The composition of claim 11, wherein the shellac is insect-derived lac.

* * * * *